United States Patent
Hu et al.

(10) Patent No.: US 11,957,712 B2
(45) Date of Patent: Apr. 16, 2024

(54) APPLICATION OF A HYDROGEL IN THE PREPARATION OF PRODUCTS FOR THE TREATMENT OF BACTERIAL INFECTIONS

(71) Applicant: Shaanxi University of Science & Technology, Xi'an (CN)

(72) Inventors: Liangbin Hu, Xi'an (CN); Haizhen Mo, Xi'an (CN); Xiaohui Zhou, Xi'an (CN); Hongbo Li, Xi'an (CN); Dan Xu, Xi'an (CN); Zhenbin Liu, Xi'an (CN); Zhen Wang, Xi'an (CN)

(73) Assignee: SHAANXI UNIVERSITY OF SCIENCE & TECHNOLOGY, Xi'an (CN)

( * ) Notice: Subject to any disclaimer, the term of this patent is extended or adjusted under 35 U.S.C. 154(b) by 0 days.

(21) Appl. No.: 18/136,350

(22) Filed: Apr. 19, 2023

(65) Prior Publication Data
US 2023/0338418 A1 Oct. 26, 2023

(30) Foreign Application Priority Data
Apr. 25, 2022 (CN) .......................... 202210438990.1

(51) Int. Cl.
| | | |
|---|---|---|
| A61K 33/26 | (2006.01) |
| A61K 9/06 | (2006.01) |
| A61K 47/22 | (2006.01) |
| A61K 47/36 | (2006.01) |
| A61P 31/04 | (2006.01) |

(52) U.S. Cl.
CPC ............... *A61K 33/26* (2013.01); *A61K 9/06* (2013.01); *A61K 47/22* (2013.01); *A61K 47/36* (2013.01); *A61P 31/04* (2018.01)

(58) Field of Classification Search
CPC .......... A61K 33/26; A61K 47/22; A61P 31/04
See application file for complete search history.

(56) References Cited

U.S. PATENT DOCUMENTS

2009/0253785 A1 10/2009 Ou

FOREIGN PATENT DOCUMENTS

| | | | | |
|---|---|---|---|---|
| CN | 102525888 A | | 7/2012 | |
| CN | 102525888 A | * | 3/2015 | ............... A61K 9/06 |
| CN | 113713855 A | * | 11/2021 | ............... B01J 31/06 |

OTHER PUBLICATIONS

Zhen Wang et al., Ferrous sulfate-loaded hydrogel cures *Staphylococcus aureus* infection via facilitating a ferroptosis-like bacterial cell death in a mouse keratitis model, Biomaterials, vol. 290, Nov. 2022, 121842 (Year: 2022).*
CN102525888A, Google English Translation document, downloaded in Sep. 2023 (Year: 2023).*
CN113713855A, Google English Translation document, downloaded in Sep. 2023 (Year: 2023).*
Xiaolin Yao et al., Iron encapsulated microstructured gel beads using an emulsification-gelation technique for an alginate-caseinate matrix, Food Funct., 2020, 11, 3811 (Year: 2020).*
Jiang Wucheng, et al., Antibiotic Tests of Ferrous Sulfate for Pathogens, Journal of Hunan Agricultural College, 1991, pp. 197-200, vol. 17, No. 2.

* cited by examiner

*Primary Examiner* — Mark V Stevens
*Assistant Examiner* — Alparslan Asan
(74) *Attorney, Agent, or Firm* — Bayramoglu Law Offices LLC

(57) ABSTRACT

An application of a hydrogel in the preparation of products for the treatment of bacterial infection is disclosed. Ferrous ion was used in the antibacterial activity test of *Staphylococcus aureus* and showed a strong bactericidal effect, which the survival rate of *Staphylococcus aureus* is less than 0.001%, as well as the survival rate of methicillin-resistant *Staphylococcus aureus* (MRSA) was less than 0.01%. Ferrous ion hydrogel was used for the treatment of keratitis and skin wound infection. Ferrous ion hydrogel for the treatment of keratitis and skin wound infection, which can significantly reduce the risk of pulmonary MRSA infection, prevented the dissimilation of MRSA to the lung, and alleviated systemic inflammation in the body in a timely and effective manner, revealing the therapeutic potential of ferrous compounds for treatment of *Staphylococcus aureus* infections, including MRSA.

1 Claim, 8 Drawing Sheets

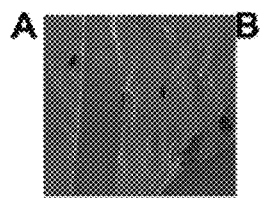 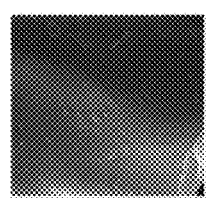  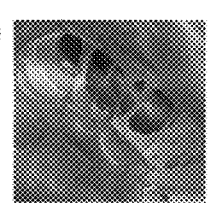
FIG. 2A     FIG. 2B     FIG. 2C     FIG. 2D
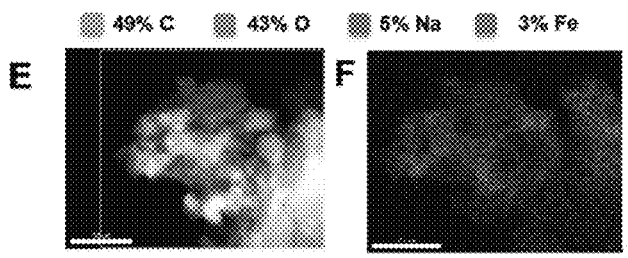
FIG. 2E     FIG. 2F
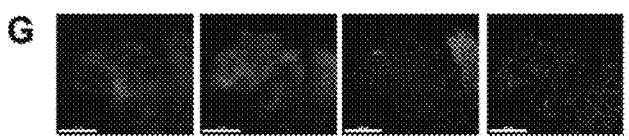
FIG. 2G
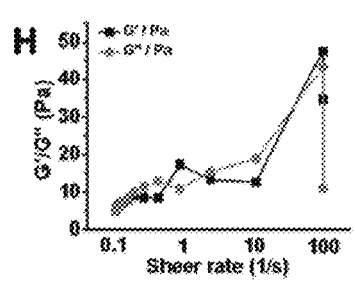 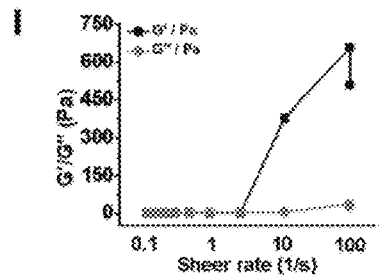
FIG. 2H           FIG. 2I

APPLICATION OF A HYDROGEL IN THE PREPARATION OF PRODUCTS FOR THE TREATMENT OF BACTERIAL INFECTIONS

CROSS REFERENCE TO THE RELATED APPLICATION

This application is based upon and claims priority to Chinese Patent Application No. 202210438990.1, filed on Apr. 25, 2022, the entire content of which is incorporated herein by reference.

TECHNICAL FIELD

The present invention relates to the field of pharmaceutical technology, and specifically to the application of a hydrogel in the preparation of products for the treatment of bacterial infections.

BACKGROUND

Keratitis is one of the common diseases in ophthalmology and one of the major blinding eye diseases in China. Infections such as bacteria, fungi, and viruses are among the most direct causes of keratitis, and when the corneal epithelium is damaged, infectious inflammation is likely to occur, especially when incorrect use of corneal contact lenses, eye contact with contaminated medications or water, etc. are likely to induce the occurrence of infectious keratitis. It is worth noting that, according to current clinical authority, the incidence of bacterial infectious keratitis caused by *Staphylococcus aureus* and *Pseudomonas aeruginosa* is still high, and the incidence is increasing year by year, therefore, the prevention of this type of keratitis needs to be concerned.

*Staphylococcus aureus* is the main culprit of common corneal and epidermal infections. However, the unregulated and abusive use of antibiotics has led to increased resistance to antibiotics, and the emergence of multi-drug resistant bacteria (e.g., methicillin-resistant *Staphylococcus aureus*, MRSA) is a serious threat to human health, and new antimicrobial therapies are urgently needed to address this crisis.

Commercially available treatment strategies for *Staphylococcus aureus* infections of keratitis and epidermal tissue are topical antibiotic eye drops, medical antibiotic hydrogels, and some essential topical steroid ointments, such as levofloxacin eye drops, vancomycin hydrogels, erythromycin hydrogels, and aureomycin ointment. The existing research shows that although antibiotics have high efficiency and low dose bactericidal effectiveness, they do not achieve the possibility of complete elimination of bacteria, however, the use of a large number of these eye drops and ointments containing antibiotics will increase the risk of bacterial resistance and make the human body drug dependent on them, forcing the dosage of drugs to increase, resulting in a vicious circle. in addition, such treatment cannot effectively prevent the migration and colonization of bacteria in the body, which may lead to lesions in other tissues and organs. Therefore, there is an urgent need to find new antibacterial materials to treat *S. aureus* infections, especially methicillin-resistant *S. aureus* (MRSA) infections.

SUMMARY

To solve the above technical problems, the present invention provides the use of ferrous ions in the preparation of products for the treatment of bacterial infections.

Application of a hydrogel in the preparation of products for the treatment of bacterial infections.

Preferably, said bacterial infection is an ocular infection or an epidermal infection.

Preferably, said bacterial infection is caused by *Staphylococcus aureus*.

Preferably, said ferrous ion is from any one of ferrous sulfate, ferrous chloride, ferrous gluconate, ferrous lactate.

Preferably, the hydrogel obtained from the ferrous compound, ascorbic acid, compound A is used for the treatment of said bacterial infection; wherein said compound A is selected from hyaluronic acid or sodium alginate.

Preferably, the concentration of said ferrous ions is $\geq 1$ μM.

Preferably, said method of preparing the hydrogel comprising the steps of:

S1, dissolving said ferrous compound and ascorbic acid in water to make a mixed solution, heating to 45-55° C., with a concentration ratio of 1:1 of ascorbic acid to ferrous compound.

S2. adding compound A during heating and stirring until a stable colloid is formed to obtain said hydrogel, the amount of addition of compound A being 2% of the mass of the mixed solution.

Preferably, the concentration of said ferrous compound is 1 mM.

A hydrogel produced by the above method.

Compared to the prior art, the present invention has the beneficial effects of.

1. The efficient bactericidal effect of the hydrogel provided by the present invention against *Staphylococcus aureus* and MRSA indicates that ferrous compounds can be used as a potential drug to combat the current antibiotic crisis.

2. The present invention selects ferrous iron sulfate, a commonly used iron supplement, as a typical representative of ferrous compounds, and studies ferrous ions as a core drug alternative to antibiotic drugs. The hydrogel was used as the carrier to successfully prepare ferrous ion hydrogel. The present invention uses ferrous sulfate as the core drug to replace antibiotic drugs, and the prepared antibacterial hydrogel of ferrous ions can effectively treat epidermal and ocular infections, and can significantly reduce the risk of pulmonary MRSA infection, and timely and effectively stop the propagation and spread of microorganisms in the body.

3. The hydrogel of the present invention is simple to prepare, but has strong material adaptability and can combine with a variety of materials such as carrageenan, xanthan gum, low acyl colloid, hyaluronic acid, carbomer, etc. to exert powerful bactericidal potential.

BRIEF DESCRIPTION OF THE DRAWINGS

FIGS. 2A-2B show SEM plots of sodium alginate hydrogels without ferrous sulfate, FIGS. 2C-2D show SEM plots of Example 2 hydrogels, FIGS. 2E-2F show XPS plots of the Example 2 hydrogel, FIG. 2G shows elemental distribution plots of the Example 2 hydrogel, FIG. 2H shows rheological properties of the sodium alginate hydrogel without ferrous sulfate, and FIG. 2I shows rheological properties of the Example 2 hydrogel.

DETAILED DESCRIPTION OF THE EMBODIMENTS

The specific embodiments of the present invention are described in detail below, but it should be understood that the scope of protection of the present invention is not limited by the specific embodiments. Based on the embodiments of the present invention, all other embodiments obtained by a person of ordinary skill in the art without creative labor fall within the scope of protection of the present invention. The experimental methods described in the embodiments of the present invention are conventional methods if not otherwise specified.

Example 1

A method for preparing a hydrogel, comprising the steps of.
S1, dissolving ferrous sulfate and ascorbic acid in sterile ultrapure water to make a mixed solution, heating to 50° C. The concentration of ferrous sulfate in this mixed solution is 1 mmol/L, and the concentration ratio of ascorbic acid to ferrous sulfate is 1:1.
S2, adding hyaluronic acid powder during the heating process, stirring until the hyaluronic acid powder dissolves and fouiis a stable gel to obtain said hydrogel, the amount of hyaluronic acid added is 2% of the mass of the mixed solution.
The hydrogel produced by the above method.

Said hydrogel is used for the application of treatment of bacterial keratitis.

Example 2

A method of preparing a hydrogel comprising the steps of
S1, dissolving ferrous sulfate and ascorbic acid in sterile ultrapure water to make a mixed solution, heating to 50° C. The concentration of ferrous sulfate in this mixed solution is 1 mmol/L, and the concentration ratio of ascorbic acid to ferrous sulfate is 1:1.
S2, adding sodium alginate powder during the heating process, stirring until the sodium alginate powder dissolves and fowls a stable gel to obtain said hydrogel, with the amount of sodium alginate added being 2% of the mass of the mixed solution.
Hydrogel made by the above method.
Said hydrogel is used for the application of treatment of skin wound infections.

Example 3

Example 3 differs from Example 1 in that the ferrous compound is ferrous chloride.

Example 4

Example 4 differs from Example 1 in that the ferrous compound is ferrous gluconate.

Example 5

Example 5 differs from Example 1 in that the ferrous compound is ferrous lactate 1 part.

Figure 8A:
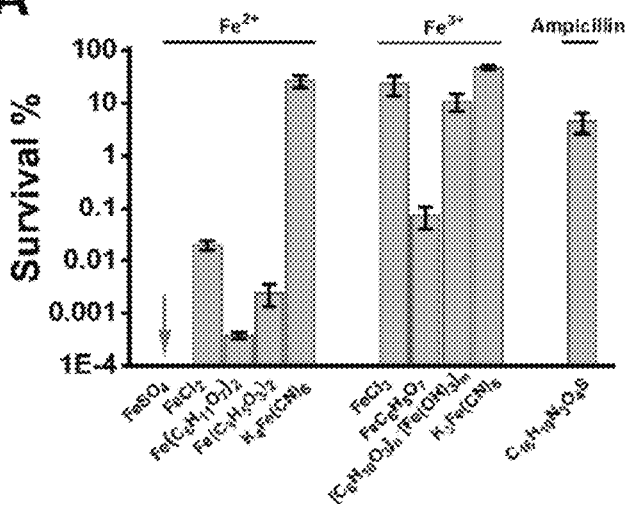
FIG. 8A is a schematic diagram of the inhibition results of nine types of iron ions against *Staphylococcus aureus*, ferrous sulfate against six pathogenic bacteria
Figure 8B:
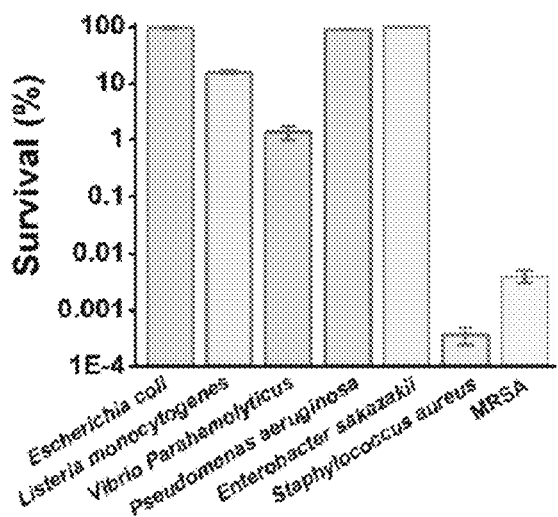
FIG. 8B is a schematic diagram of the antibacterial effect of ferrous sulfate on *Staphylococcus aureus*.

To verify the antibacterial activity of ferrous ions against *Staphylococcus aureus*, the following tests were done:
1. 5 of ferrous salts including ferrous sulfate, ferrous chloride, ferrous gluconate, ferrous lactate, potassium ferricyanide and 4 of ferrous salts including ferric chloride, ferric citrate, potassium ferricyanide were configured to a final concentration of 100 µM. 96-well plate method was used to test the drug sensitivity of 9 ferrous salts against *Staphylococcus aureus* (approximately $10^8$ CFU/mL). After 12 h treatment, the total number of bacterial colonies was determined followed by drop plate method to further investigate the antibacterial effect of iron ions on *Staphylococcus aureus*.
RESULTS: The results showed that the inhibition effect of 5 different $Fe^{2+}$ salts on *S. aureus* was much higher than that of $Fe^{3+}$ salts at the same concentration (100 µM), indicating that ferrous ions play an important role in the killing process of *S. aureus* (FIG. 8A). In particular, ferrous sulfate ($FeSO_4$) was able to inhibit the growth of almost 100% of *S. aureus*. This shows that $Fe^{2+}$ can effectively inhibit the growth of *Staphylococcus aureus*.
2. Ferrous sulfate aqueous solutions were configured to a final concentration of 16 µM; and prepare $10^8$ CFU/mL of *Escherichia coli, Listeria monocytogenes, Vibrio Parahemolyticus, Enterobacter sakazakii, Staphylococcus aureus* and MRSA. A 96-well plate assay was performed to determine the susceptibility of six pathogenic bacteria to ferrous sulfate, and after 12 h treatment, the total number of bacterial colonies was determined in a drop-plate assay to further investigate the effect of ferrous ions on their inhibition.
RESULTS: The ferrous sulfate with the best bactericidal effect was further selected as the iron agent for the study, and 6 different pathogenic bacteria were tested for their drug susceptibility. As shown in FIG. 8B that 16 µM ferrous sulfate exhibited a strong bactericidal effect against all pathogens, indicating that ferrous ions have broad-spectrum bactericidal efficacy and can effectively kill common infection-inducing pathogens. It is noteworthy that ferrous sulfate has a significantly better bactericidal effect on *S. aureus* than other pathogenic bacteria (*E. coli, Listeria monocytogenes, Vibrio parahaemolyticus*, and *Enterobacter sakazakii*), with a survival rate of less than 0.001%. It is noteworthy that ferrous sulfate also exhibited excellent antibacterial activity against methicillin-resistant *Staphylococcus aureus* (MRSA), with less than 0.01% survival after 16 µM ferrous sulfate treatment.

3. Ferrous sulfate aqueous solutions were configured to final concentrations of 1, 4, 16, and 64 µM, respectively, and ampicillin and vancomycin as positive controls were configured to 100 µg/mL, as well as ultrapure water without ferrous sulfate was set as a blank control group. Then $10^8$ CFU/mL of *S. aureus* and MRSA were prepared. The cell suspensions were added with $FeSO_4$ at final concentrations of 0, 1, 4, 16, 64 µM, respectively, and incubated at 37° C. 200 rpm for 12 h. MBC was defined as the lowest concentration of $FeSO_4$ required to kill 99.99% cells of *S. aureus*. After incubation, *S. aureus* cells were collected by centrifugation, suspended in 1 mL of normal saline solution, and subjected to 10-fold serial dilutions. Finally, 6 dilutions of each condition were plated on TSB agar, and the colony form units (CFU) were enumerated after incubation at 37° C. overnight.

Figure 8C:
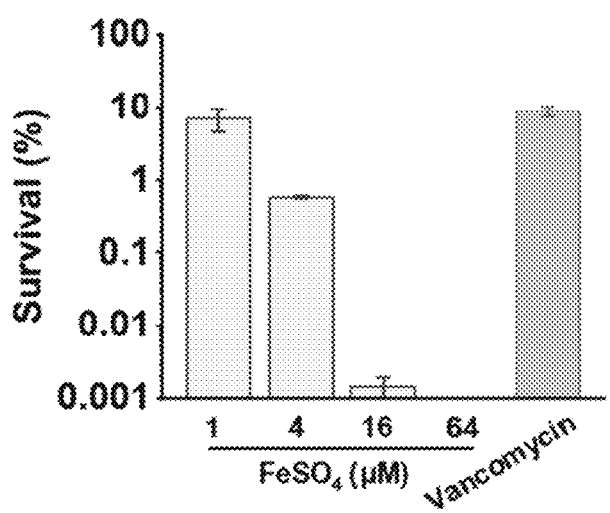
FIG. 8C is a schematic diagram of the antibacterial effect of ferrous sulfate on *Staphylococcus aureus*.

RESULTS: As shown in FIG. 8C, the results showed that the ferrous sulfate treated *S. aureus* was not able to regrow by plate reculture, indicating that the bacteria were probably dead and the degree of death was closely related to the concentration of ferrous sulfate. The MBC value of ferrous sulfate for *S. aureus* was 16 µM, and the bactericidal rate could reach 99.99% at this concentration, which has good application prospects.

In order to verify the performance of the hydrogel of the present invention, the following analysis was performed.

Ampicillin and Vancomycin used in the test were sold from Sigma-Aldrich.

I. The Distribution of Ferrous Ions in the Hydrogel

The Example 1 hydrogels and Example 2 hydrogels were placed in disposable petri dishes and were freeze-dried for 72 h, respectively and ground to powder with liquid nitrogen.

(1) Analysis of the elemental active ingredients in the hydrogel by X-ray photoelectron spectroscopy (XPS);
(2) Analysis of the phenotypic structure of the hydrogel by field emission scanning electron microscopy (SEM);
(3) Analysis of the rheological properties of the hydrogels by rotational rheometry: Rheological properties of hydrogels were analyzed by a rheometer (AR-2000, TA Company, England) using a 40 mm plate geometry with a gap of 1000 µm. Prior to the test, a thin film of silicon oil was spread around the trap to eliminate the effect of moisture evaporation. The equilibration time was set for 7 min to enable hydrogel to reach a steady state. Viscosity was tested with shear rate of 0.1-100 l/s. Unless otherwise stated, the test temperature was 37° C.

The SEM images showed that the hydrogels loaded with ferrous ions have non-homogeneous surfaces and porous structures, which facilitate the retention of water in the hydrogels and the diffusion and release of $Fe^{2+}$ from the hydrogels; the comparison of the rheological properties of the two hydrogels shows that The comparison of the rheological properties of the two hydrogels showed that the G' (modulus of elasticity) and G" (modulus of loss) of the hydrogel loaded with ferrous ions could recover to 100% within a few seconds at high shear rates, indicating that the $FeSO_4$-loaded hydrogel has the potential mobility and resilience for drug diffusion. The potential fluidity and resilience of the $FeSO_4$-loaded hydrogels were demonstrated.

The above results indicate that the hydrogels loaded with ferrous ions have potential medical applications.

II. Analysis of the Release Rate of Ferrous Ions in Hydrogels (1) 10 ml of Example 1 hydrogel and Example 2 hydrogel was injected into dialysis bags (8000-14000 Da).
(2) The dialysis bag was placed into 100 mL ultrapure water and stirred at 37° C., 200 rpm for 12 h
(3) The ferrous ions content of the dialysates was measured with O-phenanthroline calorimetric method every 30 min.

Figures 1A, 1B:
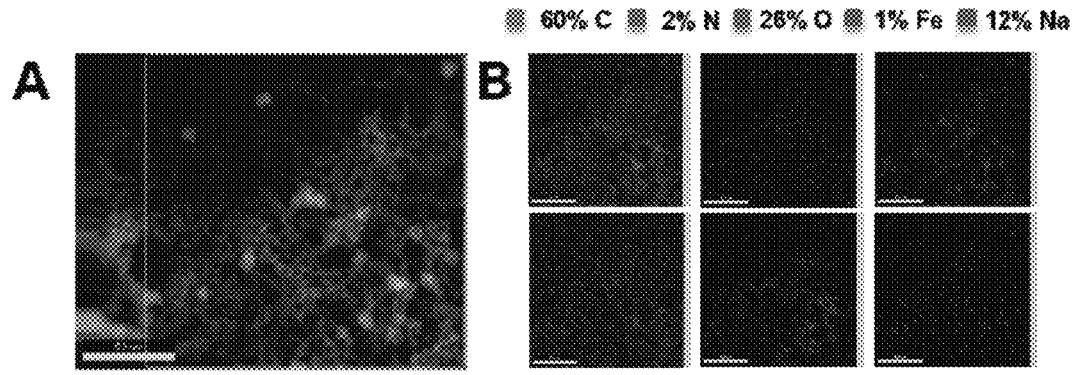
FIG. 1A shows a TEM of an Example 1 hydrogel.
FIG. 1B shows an elemental distribution of an Example 1 hydrogel.
Figures 1C, 1D:
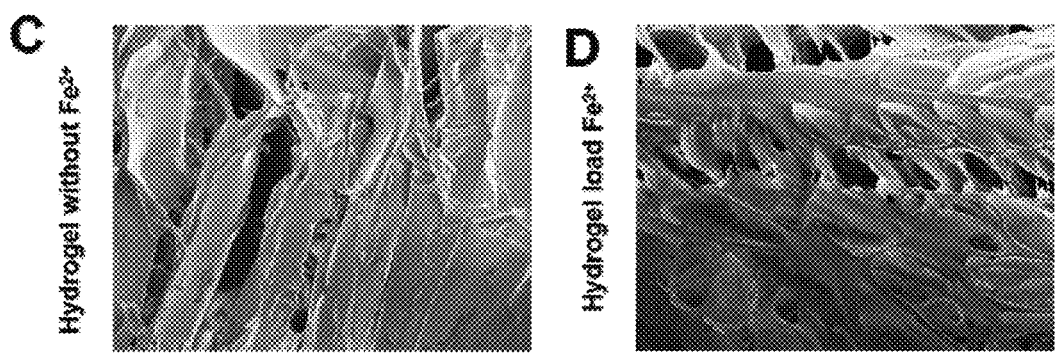
FIG. 1C shows a SEM of a hyaluronic acid hydrogel without ferrous sulfate.
FIG. 1D shows a SEM of an Example 1 hydrogel.
Figures 1E, 1F:
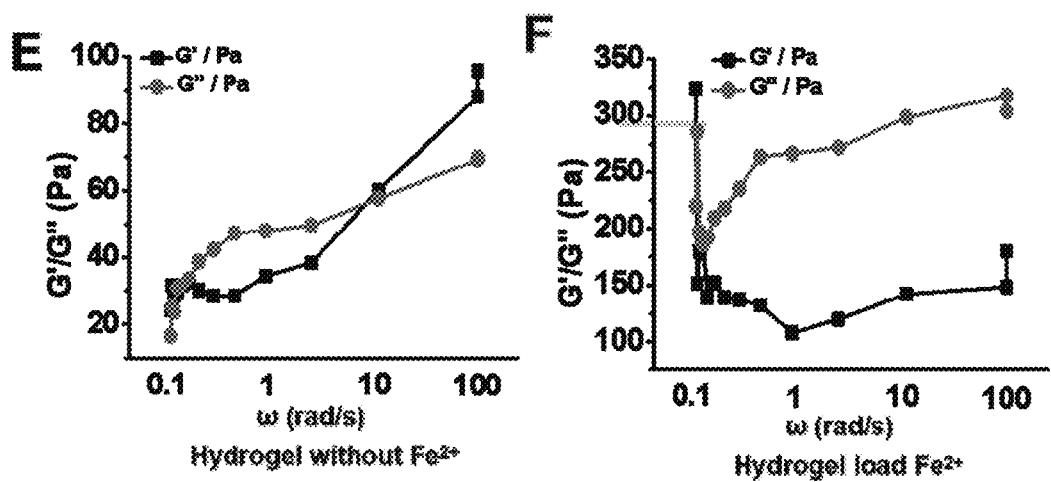
FIG. 1E shows a rheological property of a hyaluronic acid hydrogel without ferrous sulfate.
FIG. 1F shows a rheological property of an Example 1 hydrogel.
Figure 3A:
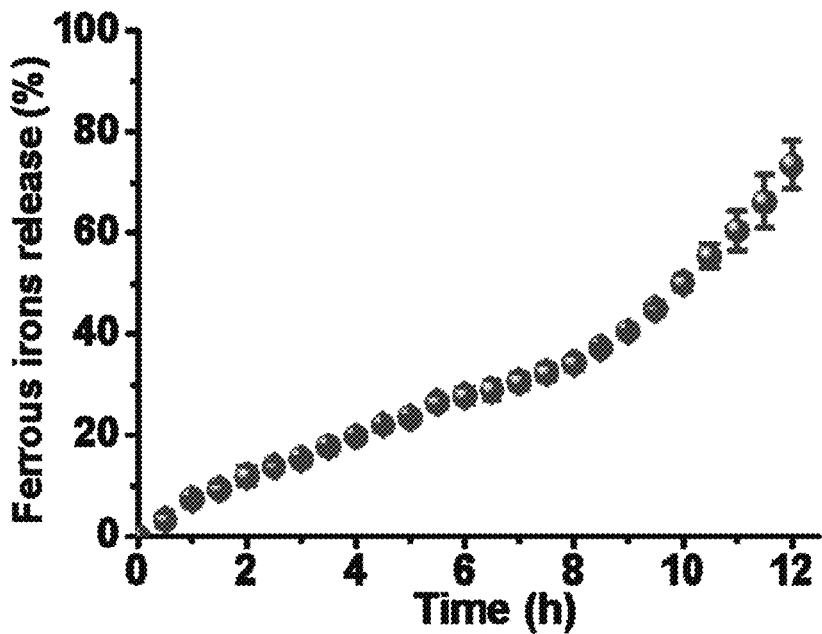
FIG. 3A shows a schematic diagram of the release rate of ferrous ions from the hydrogel of Example 1 and FIG. 3B shows a schematic diagram of the release rate of ferrous ions from the hydrogel of Example 2.
Figure 3B:
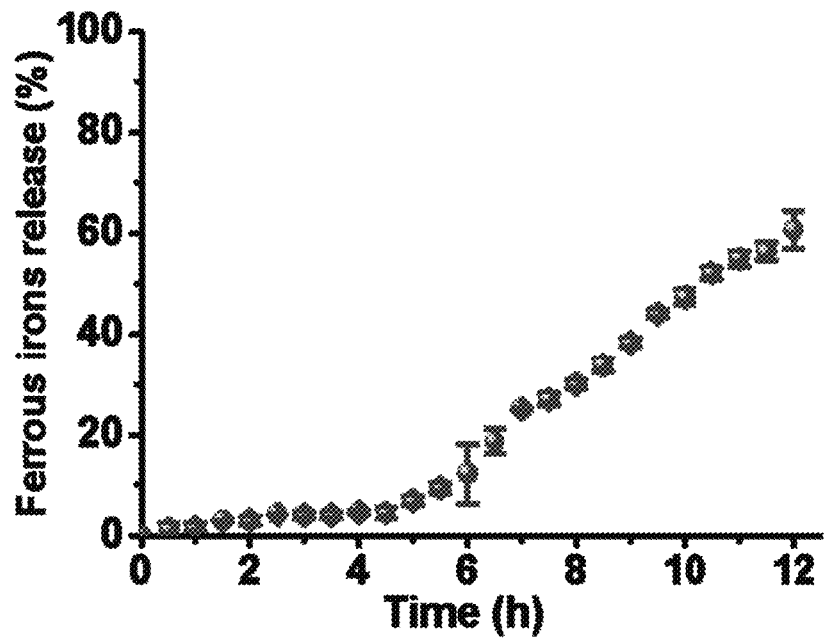

RESULTS: $Fe^{2+}$ release assay confirmed that $Fe^{2+}$ was able to be released from hydrogels in a time-dependent manner (FIGS. 3A-3B). $FeSO_4$-loaded hydrogels have the characteristics of slow and long-term release of $Fe^{2+}$, with approximately of 78.3% and 73.6% of ferrous ions after 12 h, respectively (FIGS. 3A-3B).

III. Analysis of the Antibacterial Activity Effect of Hydrogels In Vitro (1) Example 1 hydrogel, Example 2 hydrogel, ferrous sulfate hyaluronic acid hydrogel, ascorbic acid hyaluronic acid hydrogel, Ampicillin hyaluronic acid hydrogel, ferrous sulfate sodium alginate hydrogel, ascorbic acid sodium alginate hydrogel, Vancomycin sodium alginate hydrogel into sterile disposable Petri dishes for use.
(2) $10^8$ CFU/mL of *S. aureus* cells were washed twice with saline, and were collected into 1 cm sterile filter paper.
(3) The side of filter with collected cells faced up and was placed on the hydrogel.
(4) After being cultured at 37° C. for 12 h, the filter paper was placed into EP tube with 1 mL normal saline solution and ultrasound far 30 s to collect the cells from the filter paper. CFU was determined by using the drop plating method.
(5) The total number of bacterial colonies was determined by the drop plate method.
(6) To determine the antibacterial mode of loaded $FeSO_4$ hydrogel, Example 1 hydrogel (100 µL) and Example 2 hydrogel (100 µL) were added to the center of the glass slides. *S. aureus* cells ($10^8$ CFU/mL) were washed twice by normal saline solution and added to the $FeSO_4$ hydrogel surface of the glass slide. After 3 h of incubation at 37° C., PI (at the final concentration of 1 µg/mL) was dropped onto the $FeSO_4$ hydrogels containing *S. aureus* cells, and then incubated at 37° C. for 20 min. Laser scanning confocal microscope was used to determine the antibacterial model of $FeSO_4$ hydrogel.

Figure 4A:
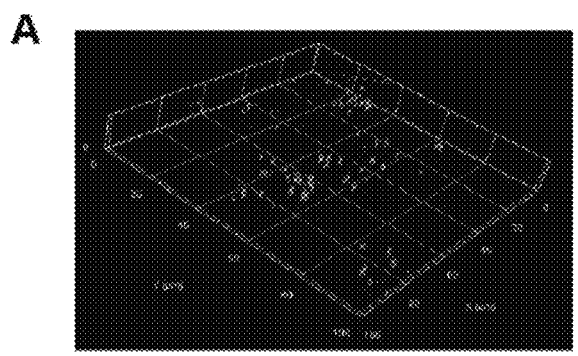
FIG. 4A is a diagram of the bactericidal distribution of Example 1 hydrogel on PI and Syto 9 stained MRSA cells.
Figure 4B:
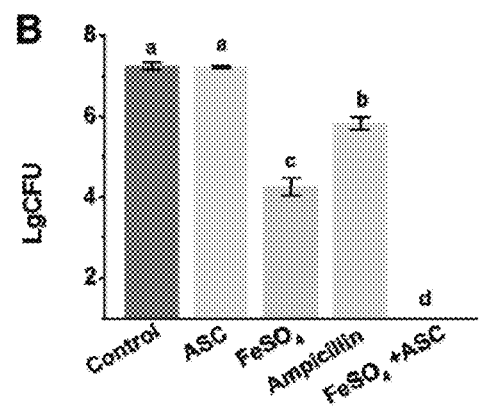
FIG. 4B is a diagram of the bactericidal activity effect of Example 1 hydrogel.

RESULTS: By simulating the in vitro surface contact between MRSA and ferrous ion hydrogel, it was found that both Example 1 hydrogel and Example 2 hydrogel had good bactericidal effect. As the FIG. 4A shown that almost all *S. aureus* cells that had contact with $FeSO_4$+ASC hydrogel were PI-positive, while all *S. aureus* cells that had contact with hydrogel without $FeSO_4$ were PI-negative. CFU enumeration showed that $FeSO_4$+ASC hydrogel killed almost 100% of MRSA cells that had direct contacted with the hydrogels. In comparison, treatment with hydrogels containing $FeSO_4$ only ($FeSO_4$ hydrogel group) only led to 3 log CFU reduction. As a control, hydrogels containing ASC only (ASC hydrogel group) had no bactericidal effect on MRSA. These results indicated that maximal bactericidal activity of $FeSO_4$-loaded hydrogel could be achieved by addition of ASC. Importantly, hydrogels containing ampicillin had much lower ability to kill MRSA.

Figure 4C:
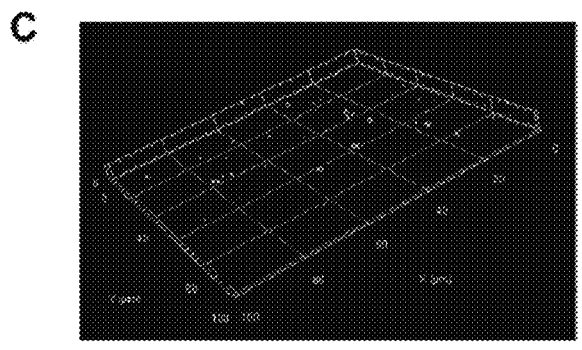
FIG. 4C is a diagram of the bactericidal distribution of Example 2 hydrogel on PI and Syto 9 stained MRSA cells.
Figure 4D:
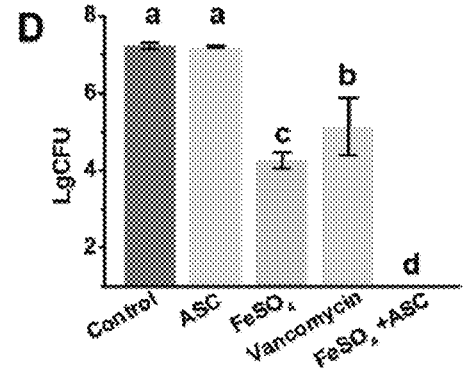
FIG. 4D is a diagram of the bactericidal activity effect of Example 2 hydrogel.

FIG. 4C shows the distribution of death of PI and Syto 9-stained MRSA cells under laser confocal microscopy after treatment with the Example 2 hydrogel, the results of which show that the hydrogel also has greater bactericidal activity, and it is clear from FIG. 4D that the hydrogel containing Vancomycin has a lower ability to kill MRSA than the Example 2 hydrogel. These results indicate that the hydrogels containing both sulfite Hydrogels of iron and ascorbic acid can be used in the treatment of MRSA infections.

IV. The Following Zoological Tests Were Pertained to Further Illustrate the Effects 1. Validation of the Effect of Example 1

(1) Preparation of *S. aureus* Cell Suspension

MRSA (from CAS) cells were cultured overnight and collected ($1\times10^8$–$1\times10^{10}$ CFU/mL), then the cells were stripped of medium and resuspended in saline.

(2) Establishment of Bacterial Keratitis Model in Mice

Mouse preparation: 40, BALB/c mice, about 8 weeks old, males.

Model Construction a. Anesthesia: mice were anesthetized by intraperitoneal injection of 0.1 mL of 1:1 mixture of 50 mg/mL ketamine and 8 mg/mL xylazine, and then fixed on a surgical corkboard. A drop of proparacaine (0.5%) was instilled in the right eye of the mice.
b. Incision: The central 3 mm area of the corneal epithelium was scarified, followed by superficial stroma incision using a 27-gauge needle.
c. Splicing: Among the 40 mice, 32 mice were inoculated with 0.1 mL of a MRSA strain ($10^8$ CFU/mL), and the remaining 8 mice were not inoculated (uninfected group).
d. Identification: Biomicroscopic examination of the mice was performed 48 h after inoculation. Blood vessel congestion, corneal clouding, and pus accumulation in the eye can be considered as successful modeling.
e. Grading was divided into two grades: mild and severe. Mild: slight opaque secretion that partially or completely covers the pupil and the anterior segment; severe: dense opaque secretion that partially or completely covers the pupil or the anterior segment, or even corneal perforation.

(3) Grouping of Animals and Administration of Drugs a. Grouping: After successful construction of the mice *S. aureus* keratitis animal model, the animals were grouped and administered into four groups of eight animals each, namely.

Blank group (8 mice): mice with scratched eyes, but not inoculated with bacteria, to which sterile saline drops were added for a total of 100 μL.

Model control group (8): constructed mouse models to which 100 μL of sterile saline was added dropwise to the eyes, followed by hyaluronic acid hydrogel treatment, for a total of 1 mL.

Treatment group 1 (8): constructed mouse models, the eyes of whose were treated with 1 mM ASC aqueous solution and 1 mM $FeSO_4$ aqueous solution, a total of 100 μL, followed by loading Example 1 hydrogel treatment, a total of 1 mL.

Treatment group 2 (8 mice): constructed mouse models whose eyes were treated with 100 μL of 1 mM ASC aqueous solution, followed by treatment with hyaluronic acid hydrogel loaded with ASC (1 mM), for a total of 1 mL.

Positive control group (8 mice): constructed mouse models whose eyes were treated with a total of 100 μL of 1 mg/mL Ampicillin (Ampicillin) followed by 1 mL of hyaluronic acid hydrogel loaded with Ampicillin (1 mg/mL).

b. Drug administration: Each group of mice was treated with the drug twice a day according to the divided groups, each time washed with saline containing the drug, followed by the hydrogel treatment, with an interval of 10 min between the two drops, for a total of 7 d.
c. Observation: Each eye was observed and recorded with a handheld flashlight before drug administration each day during the experiment. The eyes of the mice were photographed and recorded daily.
d. Ocular colony counting: gently apply sterile saline wet cotton balls to the upper and lower eyelids and then put into the inner 5 mL of sterile saline, mix well, extract 100 μL, dilute in a gradient, drop the plate, incubate and count.
e. Blood index assay: detect and identify the type and number of bacteria in the blood, and detect relevant blood indexes
f. Lung colony counting: mice were executed after 7 d of treatment, and the lungs of mice were dissected and removed, placed in 5 mL PBS, sonicated, mixed, and the supernatant was aspirated at 100 μL, diluted in a gradient, dropped onto a plate, incubated and counted.
g. Histopathological examination of the eye: mice were executed after 7 d of treatment, and the eyes were removed, fixed in 10% formalin, embedded in paraffin, stained with HE, and examined by light microscopy to observe the pathological histological changes.

Figure 5A:
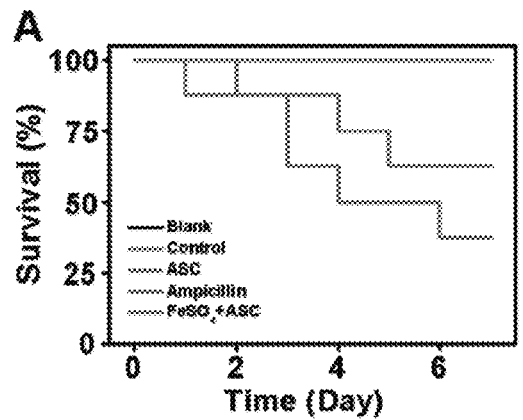
FIG. 5A shows a schematic diagram of the survival rate of mice in different treatment groups.
Figure 5B:
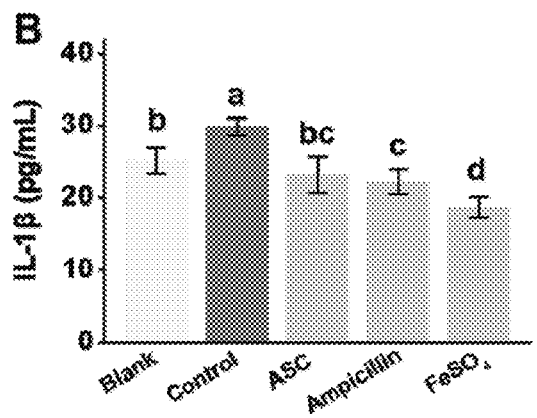
FIG. 5B shows a schematic diagram of the change of inflammatory factor IL-1 in mice in different treatment groups.
Figure 5C:
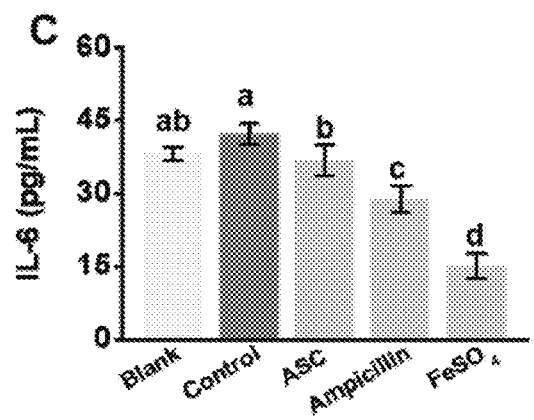
FIG. 5C shows a schematic diagram of the change of inflammatory factor IL-6 in mice in different treatment groups.
Figure 6A:
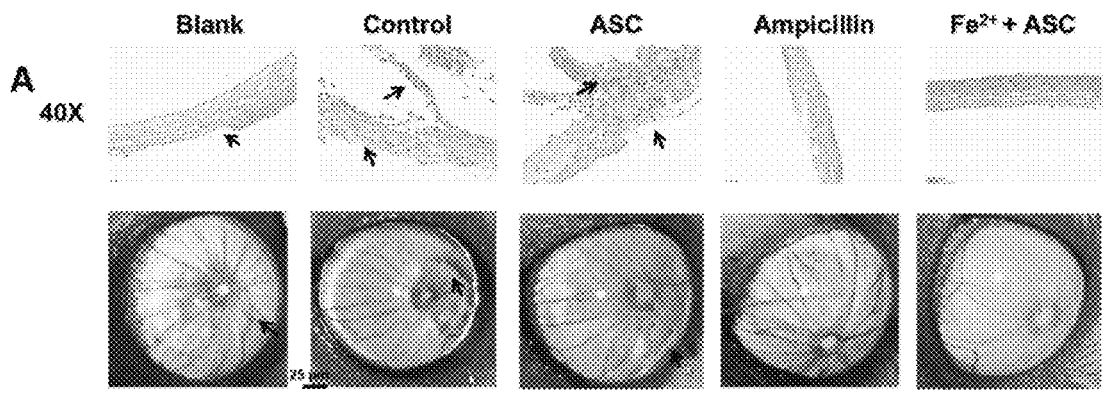
FIG. 6A shows the results of histological sections of mouse eye and the general picture after treatment in each group and FIG. 6B shows the results of histological sections of mouse lung and the general picture after treatment in each group.
Figure 6B:
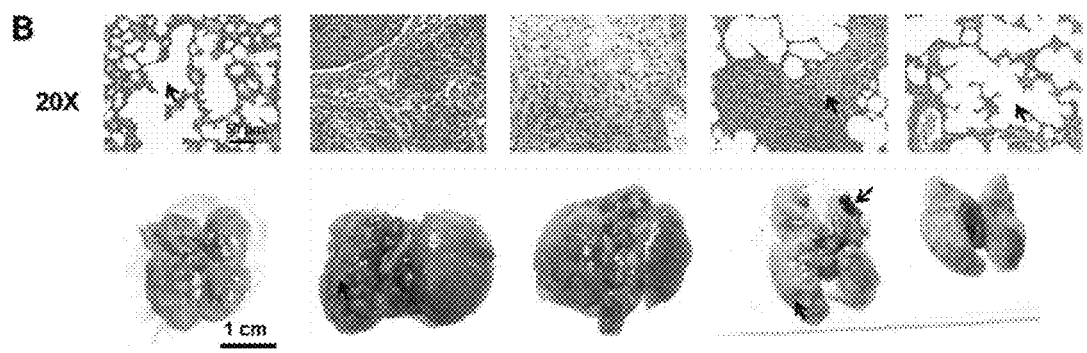

RESULTS: After treating the eyes of MRSA-infected mice with Example 1 hydrogel for 7 days at 48 h post-infection, the survival rate, cellular inflammatory factors, and pathological sections of the eyes and lungs were analyzed to assess the bactericidal activity of the self-administered ferrous hydrogel, as shown in FIG. 5A. The survival rate of $FeSO_4$+ASC hydrogel was significantly higher than that of the control hydrogel group, which was 100%. Meanwhile, the serum cytokine and IL-6 levels in the uninfected control group were 25 pg/mL and 35 pg/mL, respectively. The levels of IL-1 and IL-6 in the ASC hydrogel-treated group were slightly lower than those in the blank hydrogel-treated group. The serum IL-1 and IL-6 levels in the ampicillin hydrogel and FeSO$_4$+ASC hydrogel groups were significantly lower than those in the blank hydrogel group, and the decrease in IL-6 and IL-1 in the FeSO$_4$+ASC hydrogel group was the most significant. It was suggested that FeSO$_4$+ASC hydrogel could reduce the inflammatory response during *S. aureus* infection, and its effect was greater than that of ampicillin hydrogel (FIGS. 5B-5C). The microscopic images and histological analysis of HE staining of mouse eyes and lungs after 7 days of treatment with different hydrogels showed that for mouse eyes, as shown in FIG. 6A, there was pus and blood secretion in the eyes of mice in the blank hydrogel group, and corneal edema was obvious, and a large number of neutrophils were visible; the corneal inflammatory cells in the mice in the ampicillin hydrogel group were significantly reduced, and the corneal thickness was normalized, however, the mice still had partial repair defects in the corneas. However, the mice still had partial repair defects; while in the self-administered ferrous hydrogel group, the mice's corneal tissue basically returned to normal: the membrane edema disappeared; there was no inflammatory reaction, and the neovascularization was reduced, which indicated that the Example 1 hydrogel had a better therapeutic effect on *Staphylococcus aureus* infection in mice. As shown in FIG. 6B, the lung damage of the mice treated with FeSO$_4$+ASC hydrogel was significantly alleviated compared with the other treatment groups, and the lung bronchi were normal in size, the alveoli were intact, and no inflammatory cells such as neutrophils and phagocytes were seen in the lungs, which were basically the same as those in the uninfected group. These results indicate that the Example 1 hydrogel has potential advantages in the treatment of keratitis, but also effectively prevents the spread of corneal infection to the lungs.

2. Validation of the Effect of Example 2

(1) Preparation of *S. aureus* Cell Suspension

MRSA (from CAS) cells were cultured overnight and collected ($1\times10^8$–$1\times10^{10}$ CFU/mL), then the cells were stripped of medium and resuspended in saline.

(2) Constructing an Animal Model of *Staphylococcus aureus* Infected Epidermal Wound in Mice Mouse preparation: 30, BALB/c mice, about 8 weeks old, males.

Model Construction a. Anesthesia: each mouse was injected intramuscularly with 0.125 mL of ketamine hydrochloride (100 mg/mL): xylazine (20 mg/mL)=1:1 mixture The substance is used for anesthesia, and the mice are observed for about 3-5 minutes to determine whether the anesthesia is successful by observing their respiratory status and heartbeat frequency (respiratory rhythm becomes slower and heartbeat frequency decreases).

b. Back trauma incision: hair removal cream was used to treat the back of mice with hair removal, saline gauze was used to scrape the back, and 75% ethanol was used to wipe the back of mice. Creating a full-length wound (10 mm×10 mm) in the skin of the back of each mouse down to the depth of the subcutaneous tissue and keeping it open, resulting in the absence of skin damage on the back of the mouse.

c. (a) Inoculation: two drops of prepared *Staphylococcus aureus* suspension ($10^8$ CFU/mL, 50 µL per drop, 100 µL total) were added to the surface of the back wound of the mice and the wound was dressed with sterile gauze.

d. Infection: observation of abscesses on the wound surface of mice after 24/48 h of inoculation treatment.

(3) Animal Grouping and Drug Administration a. Grouping: after the successful construction of the mouse *Staphylococcus aureus* infection epidermal trauma animal model, the animals were grouped and administered into 5 groups of 6 animals each, namely.

Blank group (6 mice): mice with a wound opening on the back but not inoculated with bacteria, and sterile saline was added to the wound drop by drop for a total of 100 µL.

Model control group (6 mice): constructed mouse model, not treated with drugs, 100 µL sterile saline added dropwise to the wound, followed by sodium alginate hydrogel treatment, 1 mL in total.

Treatment group 1 (6 mice): constructed mouse models, treated with 1 mM ASC aqueous solution and 1 Mm FeSO$_4$ aqueous solution, 100 in total, to wounds, followed by hydrogel treatment loaded with Example 2, 1 mL in total.

Treatment group 2 (6 mice): constructed mouse models whose wounds were treated with 100 µL of 1 mM ASC aqueous solution, followed by hydrogel treatment with sodium alginate loaded with ASC (1 mM), for a total of 1 mL.

Positive control group (6 mice): the constructed mouse models were treated with 100 µL of 1 mM vancomycin (vancomycin) in aqueous solution and then treated with sodium alginate hydrogel loaded with vancomycin for 1 mL.

b. Drug administration: each group of mice is treated separately according to the divided groups, twice a day, each time by washing with saline containing the drug, followed by hydrogel treatment, with an interval of 10 min between treatments, followed by wound dressing with sterile gauze again, for a total of 3 d.

c. Observation: each mouse wound should be observed and recorded with a handheld flashlight before drug administration every day during the experiment. And daily photographs were taken to record the wound healing in mice.

d. Wound surface colony count: use sterile saline wet cotton ball to gently apply the wound surface into 5 mL of sterile saline inside, mix well, extract 100 µL, dilute in gradient, drop plate, culture and count.

e. Blood index test: detect and identify the type and number of bacteria in the blood, and test the relevant blood index f. Lung colony counting: mice were executed after 7 d of treatment and the lungs were dissected and removed, placed in 5 mL of PBS, sonicated, mixed, aspirated 100 of supernatant, diluted in a gradient, drip-plate, cultured and counted.

Figure 7A:
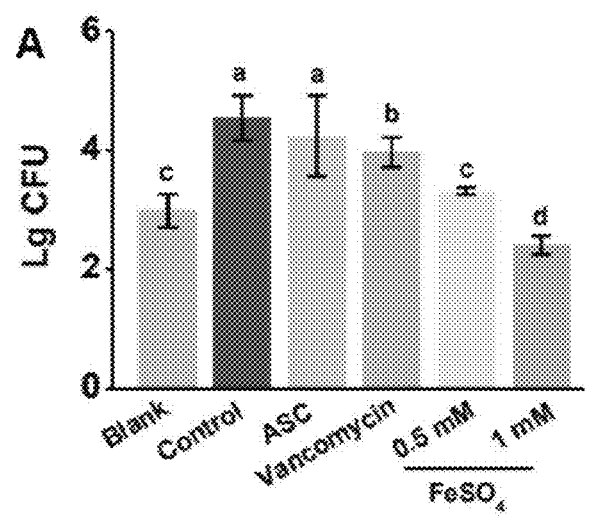
FIG. 7A shows a schematic diagram of the number of bacteria in the lungs of infected mice after 3 days of hydrogel treatment and FIG. 7B shows a gross picture of wound healing in mice.
Figure 7B:
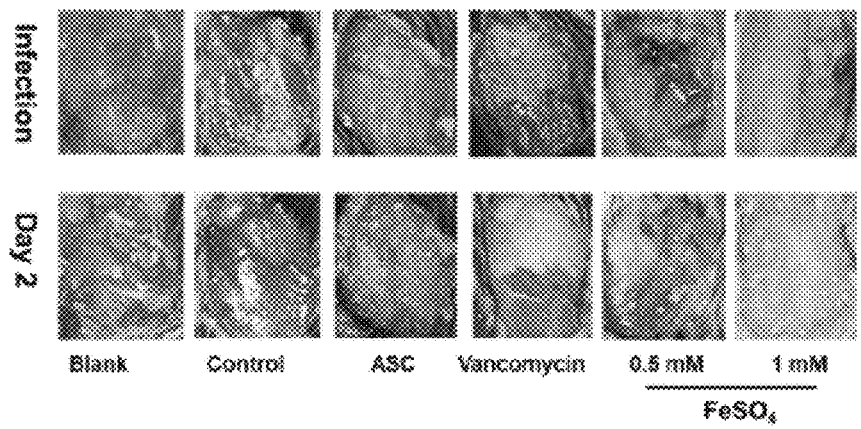

RESULTS: *Staphylococcus aureus* is a common human pathogen, and bacterial infections are most common in clinical practice. in particular, methicillin-resistant *Staphylococcus aureus* infections can cause septic skin infections that are severely life-threatening. Therefore, an important indicator to assess the potential application of FeSO$_4$ is the great ability of MRSA cells to clear from wounds and to promote wound healing. As shown in FIG. 7B, the mouse epidermal infection model observed that the wound healing ability of the Example 2 hydrogel-treated group was superior to the other groups at day 3, and a small amount of pus remained on the wound in the uninfected treatment group. In the other five MRSA-infected groups, the sodium alginate hydrogel with ASC only and the vancomycin hydrogel treatment group failed to effectively ease wound healing, with severe pus and blood on the wound surface, compared to the vancomycin hydrogel group, the Example 2 hydrogel facilitated wound healing, with no pus and blood on the wound surface and a smaller wound area than that on day 0. Dissection of the lungs of mice in each treatment group for *S. aureus* testing revealed that $FeSO_4$–ASC hydrogel eliminated at least 99.9% of MRSA cells as shown in FIG. 7A, while the bactericidal effect of the remaining treatment groups was significantly weaker than that of the ferrous hydrogel, and FeSO4 hydrogel epithelial treatment had a potential preventive effect on the infection of MRSA cells to the lungs.

Thus, it was confirmed that $FeSO_4$-containing hydrogels have potential antimicrobial activity against microbial resistance in vivo.

It is to be noted that when the claims of the present nvention relate to ranges of values, it is to be understood that two endpoints of each range of values and any of the values between the two endpoints may be chosen, and to prevent redundancy, the present invention describes preferred embodiments.

Although preferred embodiments of the invention have been described, those skilled in the art may make additional changes and modifications to these embodiments once the basic creative concepts are known. Therefore, the appended claims are intended to be construed to include the preferred embodiments and all changes and modifications that fall within the scope of the present invention.

It is clear that those of skill in the art can make various changes and variations to the invention without departing from the spirit and scope of the invention. Thus, to the extent that such modifications and variations of the present invention fall within the scope of the claims of the present invention and their technical equivalents, the present invention is also intended to encompass such modifications and variations.

What is claimed is:

1. A method of preparing a hydrogel for a treatment of a bacterial infection, wherein the bacterial infection is an ocular infection or an epidermal infection caused by methicillin-resistant *Staphylococcus aureus*;
   the hydrogel is prepared from ferrous sulfate, ascorbic acid, and hyaluronic acid;
   the method of preparing the hydrogel comprises steps of:
   S1, dissolving the ferrous sulfate and the ascorbic acid in water to make a mixed solution and heating the mixed solution to 45-55° C., wherein a concentration ratio of the ascorbic acid to the ferrous sulfate is 1:1;
   S2, adding the hyaluronic acid during a heating process and stirring until a stable colloid is formed to obtain the hydrogel, wherein an amount of the hyaluronic acid added is 2% of a mass of the mixed solution,
   wherein the mixed solution in S1 includes 1 mM ferrous sulfate.

* * * * *